United States Patent [19]
Lanza et al.

[11] Patent Number: 5,891,477
[45] Date of Patent: Apr. 6, 1999

[54] NON-STEROIDAL ANTI-INFLAMMATORY AGENTS INHIBITION OF FIBROTIC RESPONSE TO AN IMPLANTED DEVICE

[75] Inventors: Robert P. Lanza, Clinton; William L. Chick, Wellesley, both of Mass.

[73] Assignee: Biohybrid Technologies, Inc., Shrewsbury, Mass.

[21] Appl. No.: 828,327

[22] Filed: Mar. 28, 1997

[51] Int. Cl.$^6$ ............................... A61F 2/02; A61K 9/50; C12N 11/04; C12N 11/08
[52] U.S. Cl. ........................ 424/501; 424/426; 424/502; 435/180; 435/182
[58] Field of Search ..................... 424/426, 501, 424/502; 435/180, 182

[56] References Cited

PUBLICATIONS

Wong, H. et al., "The Microencapsulation of Cells Within Alginate Poly–L–Lysine Microcapsules Prepared with the Standard Single Step Drop Technique: Histologically Identified Membrane Imperfections and the Associated Graft Rejection", *Biomat. Art. Cells & Immob. Biotech.*, vol. 19 (4), pp. 675–686 (1991).

Young, D., "Inverted Microcarriers: Using Microencapsulation to Grow Anchorage–Dependent Cells", *Fundamentals of Animal Cell Encapsulation and Immobilization*, CRC Press, Chapter 11, pp. 243–265 (1993).

Young, D. et al., "Inverted Microcarriers Using Microencapsulation to Grow Anchorage–Dependent Cells in Suspension", *Biopharm*, vol. 2, pp. 34–46 (1989).

*Primary Examiner*—Carlos A. Azpuru
*Attorney, Agent, or Firm*—Fish & Richardson P.C.

[57] ABSTRACT

Methods for inhibition of fibrotic rejection of implanted devices which contain cells by administering to the recipient of the devices an amount of a non-steroidal anti-inflammatory agent (NSAID) sufficient to inhibit fibrotic inactivation of the device. Most NSAID's are carboxylic acids (R—COOH) or enolic acids (R—COH).

30 Claims, No Drawings

NON-STEROIDAL ANTI-INFLAMMATORY AGENTS INHIBITION OF FIBROTIC RESPONSE TO AN IMPLANTED DEVICE

The invention relates to methods of suppressing a subject's fibrotic response to a device implanted in the subject.

BACKGROUND OF THE INVENTION

Transplantation of donor tissue into a recipient can be used to treat a wide variety of disorders, including heart disease, neoplastic disease, and endocrine disease. The clinical application of transplantation-based therapies are, however, limited by several factors. These factors include immune rejection of transplanted allogeneic or xenogeneic tissue by the transplant recipient, a shortage of allogeneic donor-tissue, and donor-propagated immune attack of recipient tissue (graft-versus-host-disease).

Immune rejection of transplanted donor-tissue can be the most serious barrier to more widespread availability of the benefits of transplantation-based therapies. Implantation of allogeneic or xenogeneic donor-tissue into an immunocompetent recipient generally results in a vigorous and destructive immune response directed against the donor-graft. Efforts to prevent immune-based destruction of donor tissue have generally fallen into two categories. In one approach, efforts have been directed to moderating the recipient's immune response, e.g., by the induction of specific immunological tolerance to transplanted tissue, or much more frequently, by the administration of broad-spectrum immune suppressants, e.g., cyclosporin. In the other major approach, efforts to prolong the acceptance of a donor-graft have been directed to rendering the donor-graft less susceptible to attack, e.g., by immunoisolating the donor-tissue by encapsulating it in a way which minimizes contact of elements of the recipient's immune system with the encapsulated donor tissue.

Immunoisolation is particularly attractive for the treatment of endocrine disorders or in hormone or enzyme replacement therapies. For example, the implantation of immunoisolated pancreatic islet cells can be used to restore glucose-responsive insulin function in a diabetic recipient. Islets can be placed in a mechanical enclosure, or can be coated with a material, which allows relatively free diffusion of glucose, insulin, nutrients, and cellular waste products but which is impervious to components of the recipient's immune system.

A microcapsule typically includes an inner core in which living cells are embedded and optionally an outer semipermeable coating. The outer coating often has a porosity which prevents components of the implant recipient's immune system from entering and destroying the cells within the microcapsule. Gel microcapsules containing a small number of living cells have been used to transplant both allogeneic and xenogeneic donor cells into recipient animals. Several methods for microencapsulating cells, e.g., pancreatic islet cells, in an alginate gel have been investigated. These include the alginate-polylysine technique described in Lim et al., U.S. Pat. No. 4,391,909 and Soon-Shiong et al., Transplantation, 54:769–774 (1992), the alginate-chitosan system described in Rha et al., U.S. Pat. No. 4,744,933, and the polyacrylate encapsulation method described in Sefton, U.S. Pat. No. 4,353,888. A tissue response to implanted microcapsules limits the usefulness of this class of therapeutic entities. The fibrotic response consists of host deposition of fibrous proteins that causes death and rejection of the encapsulated therapeutic substance. Immunosuppressive drugs have been used to delay rejection, for example, fetal nigral allograft survival and function has been shown for up to 10 months after transplantation and immunosuppression (with the agents cyclosporin, azathioprine, and prednisone) in a human Parkinson's patient. (Widner et al., (1991) *Transplant. Proc.*, 23:793). Function of islet cells implanted in polyalginate microcapsules was extended for a period approximately 4-fold that of the control by administration of cyclosporin A (CsA, 20–30 milligrams/kg/day, s.c.; Langa, Ed. R.G. Landes, Press 1994, Texas, *Immunomodulation of Pancreatic Islets*). However, a variety of negative side effects of CsA include nephrotoxicity, increased incidence of viral diseases, and transient liver dysfunction. Drugs that are safe, economical, and convenient for suppression of fibrotic rejection of implanted devices are clearly needed.

Unless otherwise defined, all technical and scientific terms used herein have the same meaning as commonly understood by one of ordinary skill in the art to which this invention belongs. Although methods and materials similar or equivalent to those herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

SUMMARY OF THE INVENTION

The inventors have discovered that non-steroidal anti-inflammatory agents NSAIDs) such as naproxen (e.g., Aleve, Anaprex, or Naprosyn) can inhibit fibrotic inactivation, by a subject, of an implantable device, without the undesirable effects which accompany the use of immunosuppressive agents.

Accordingly, the invention features, a method inhibiting a subject's fibrotic response to a device implanted in the subject. The method includes: administering an effective amount of a NSAID to the subject, thereby inhibiting fibrotic inactivation of the device.

In preferred embodiments the device includes a cell or tissue. The cell or tissue can be from an animal other than the subject. The cell or tissue can be allogeneic or xenogeneic with regard to the subject. The cell or tissue can be from a species which is concordant or discordant with the subject. The cell or tissue can be from the subject, but if it is from the subject, it is preferably genetically engineered to express a substance not normally expressed by or on that cell or tissue.

In preferred embodiments the subject is a human and the cell or tissue is from a second species, e.g., a discordant species, e.g., a discordant vertebrate, e.g., a dog, pig, goat, rabbit goat, horse, cow, or sheep.

In preferred embodiments the subject is a human and the second species is a non-human primate species.

In preferred embodiments the cell is a pancreatic islet cell. In preferred embodiments, the pancreatic islet is from a dog, pig, goat, rabbit goat, horse, cow, sheep, or a non-human primate. In preferred embodiments, the pancreatic islet is from a pig. In preferred embodiments, the pancreatic islet is from a human other than the subject.

In preferred embodiments, the cell or tissue is genetically engineered.

The cell or tissue can be from the pancreas, adrenal gland, brain, kidney, liver, thymus parathyroid or thyroid. In a preferred embodiment the cell is a cultured cell. In a preferred embodiment, the cell is from a primary culture. In a preferred embodiment, the cell has been treated with a cytokine or a growth factor.

In preferred embodiments: the cell is an immortalized cell; the cell is a blood cell; the cell or tissue is a fetal; the cell is a skin, astroglial, or myoblast cell.

In preferred embodiments the device is a microcapsule. The microcapsule can contain a cell or tissue, e.g., a cell or tissue which is a source of a therapeutic substance. The microcapsule can include a gel member, e.g., a shape-retaining gel member, in which a cell or tissue is embedded. The gel can be a hydrogel. In preferred embodiments the hydrogel includes agarose or alginate. The agarose or alginate can have a higher number of guluronic acid than mannuronic acid monomers. The microcapsule can include a semipermeable membrane or coating, e.g., a semipermeable coating which surrounds a gel component, e.g. a gel core in which a cell or tissue is embedded. The semipermeable membrane can include a polymer, e.g., a positively charged polymer. By way of example, the positively charged polymer can be a polyamino acid. In preferred embodiments, the positively charged polymer includes lysine or ornithine. In a particularly preferred embodiment, the positively charged polymer is polylysine or another polymer of one or more positively charged amino acids. In preferred embodiments the coating can include chitosan.

In preferred embodiments the NSAID: is a carboxylic acid or an enolic acid; is a pyrazolone or a xicam; is a salicylate, a proprionate, an anthranilate or a phenylacetate.

In another aspect, the invention features, a method of inhibiting fibrotic inactivation, by a subject, of an implantable microcapsule which includes a xenogeneic cell embedded in a gel core which is enclosed with a semipermeable membrane. The method includes: administering an effective amount of a non-steroidal anti-inflammatory agent, thereby inhibiting inactivation. In preferred embodiments, the non-steroidal anti-inflammatory agent comprises administration of at least one of the group consisting of aspirin, naprosyn, and acetaminophen.

In another aspect, the invention features, a kit which includes an NSAID and instructions for using an NSAID to reduce fibrotic inactivation of an implantable device. In preferred embodiments, the NSAID is a carboxylic acid or an enolic acid. Examples of the carboxylic acid include a pyrazolone or a xicam. Examples of the enolic acid include a salicylate, a proprionate, an anthranilate or a phenylacetate.

The methods of the invention allow the control of fibrotic responses to implants with little or no immunosuppression.

Other features and advantages of the invention will be apparent from the following detailed description and from the claims.

DETAILED DESCRIPTION

Non-steroidal anti-inflammatory agents

Non-steroidal anti-inflammatory agents (NSAIDs) include numerous compounds of diverse chemical structure. Most if not all are believed to share a common mechanism of action, and almost all are weak organic acids. This large group of compounds can be divided into two main groups, carboxylic acids (R—COOH) and enolic acids (R—COH). Further subdivisions based on chemical structure can be made. The main groups of enolic acids are the pyrazolones, such as phenylbutazone, oxyphenbutazone, dipyrone and isopyrin, and the xicams, which include piroxicam and miloxicam. Carboxylic acid subgroups comprise the salicylates, e.g. acetylsalicylate (aspirin); propionic acids, e.g. ibuprofen and naproxen; anthranilic acids, e.g. meclofenamic acid; phenylacetic acids, e.g. acetaminophen; aminonicotinic acids, e.g. flunixin; and indolines, e.g., indomethacin.

Commonly used NSAIDs, with brand names, generic names, standard sizes of doses, and chemical structures, include: Advil, ibuprofen, 200 mg (±)-2-(p-isobutylphenyl) propionic acid; Aleve, naproxen, 250, 375, and 500 mg, 2-naphthaleneacetic acid, 6-methoxy-α-methyl-, (+); Anaprex, naproxen, 275 mg, 2-naphthaleneacetic acid, 6-methoxy-α-methyl-, sodium; Ansaid, flurbiprofen, 50 and 100 mg, [1,1'-biphenyl]-4-acetic acid, 2-fluoro-alphamethyl-, (±); Butazolidin, phenylbutazone, 100 mg, 4-butyl-1,2-diphenyl-3,5-pyrazolidinedione; Clinoril, sulindac, 150 and 250 mg, (Z)-5-fluoro-2-methyl-1-[[p-(methylsulfinyl)phenyl]methylene]-1H-indene-3-acetic acid; Dolobid, diflunisal, 250 and 500 mg, 2'4'-difluoro-4-hydroxy-3-biphenylcarboxylic acid; Indocin, indomethacin, 25 and 50 mg, 1-(4-chlorobenzoyl)-5-methoxy-2-methyl-1H-indole-3-acetic acid; Motrin, ibuprofen, 300, 400, 600, 800 mg, see Advil supra for chemical structure; Midol-PMS, acetaminophen, 500 mg; Tylenol Extra Strength, acetaminophen, 500 mg; Meclomen, meclofenamate, 50 and 100 mg, N-(2,6-dichloro-M-tolyl)anthranilic acid, sodium salt, monohydrate; Nalfon, fenoprofen calcium as dihydrate, 200 mg and 300 mg, derivative of arylacetic acid; Naprosyn, naproxen, 250, 375, and 500 mg, 2-naphthaleneacetic acid, 6-methoxy-α-methyl-, (+); Orudis, ketoprufen, 25, 50, and 75 mg, 2-(3-benzoylphenyl)-propionic acid; Ponstel, mefenamic acid, 250 mg, N-(2,3-xylyl)-anthranilic acid; Voltaren, diclofenac sodium, 25, 50 and 75 mg, sodium [o-[(2,6-dichlorophenyl)amino]phenyl]acetate; Disalcid, salsalate, 500 mg, 2-hydroxy-benzoic acid 2-carboxylphenyl ester, also Monogesic and Salflex; Rowasa, mesalamine, rectal suspension enema, provided to deliver 2 to 4g per day in divided doses, 5-amino-salicylic acid; and aspirin, acetylsalicylic acid, 325 mg and 650 mg.

For those NSAIDs for which the mechanism of action is known, most have been found to inhibit the formation of arachidonic acid metabolites through suppression of cyclooxygenase and lipoxygenase pathways and thus lead to a reduction in inflammation mediated by these metabolites. Cyclooxygenase converts arachidonic acid to the cyclic endoperoxides, $PGG_2$ and $PGH_2$ (known as PGs). By action of further specific enzymes, these compounds are converted to different members of the family of inflammatory mediators, the eicosanoids, which includes $PGE_2$ and $PGI_2$. However, the structure of cyclooxygenases varies among tissues, and NSAIDs differ in their ability to combine with each of these enzymes, which explains differences in potency and species responses.

NSAIDs useful in methods of the invention should have no immunosuppressive activity at the dosage used. Immunosuppressive activity, as used herein, refers to inhibiting or decreasing the ability of B and T cells to react to antigenic stimulation by cell-mediated responses and by elaboration of antibodies. NSAIDs should not diminish interleukin activities, which are known to trigger fibroblastic proliferation and the cascade that leads to fibrosis. NSAIDs should diminish PG synthesis. PGs are cytostatic agents. As reduction in PG synthesis would be anticipated to increase fibrotic proliferation, the results described herein are unexpected.

Preferred NSAIDs include but are not limited to acetylsalicylate (aspirin), acetaminophen, indomethacin, ibuprofen, and naproxen.

A candidate NSAID can be tested for suitability for use in the invention by implanting microcapsules or devices containing pancreatic islet cells in a heterologous animal, for example, in dogs, rodents, or simians, for one or two or more days, removing the microcapsules, and testing them for ability to respond to glucose in vitro. A simple assay for in vitro glucose response can be performed by measuring the ability of microcapsules to secrete insulin in response to altered levels of glucose in media supplied in vitro, for example, at basal (50 mg/dl glucose) and at stimulatory (300 mg/dl glucose) levels. Functional microcapsules should exhibit a four- to five-fold increase in insulin secretion which can be sustained for one hour. Further, insulin secretion should return to basal levels after perfusion with low glucose solution.

Administration of NSAIDs

Preferred NSAIDs are available on a non-prescription basis for human administration. Initial doses for trials with non-human mammals, which are used in the present invention to screen or test novel NSAIDs for efficacy in suppression of fibrotic response to microsphere implants, can be obtained by normalizing the dose for human use of active constituent (e.g., 200 milligrams of ibuprofen per 100 kg human) to the weight of the animal (for example, 30 milligrams to be administered to a 15 kg small dog; one milligram to a 500 g rat). Sustained NSAID dose schedules for animal subjects can include consideration of the pharmacokinetics of the species, to account for example, for differences in pharmacokinetics of clearance. The $t_{1/2}$ for clearance of naprosyn, for example, is approximately threefold longer for the dog than for the human, so that less frequent and lower relative doses are necessary to sustain a therapeutic naprosyn blood level in the dog. Thus, 10 mg rather than 30 mg of naprosyn can be an effective dose for a small dog.

Doses for the human patient can be repeated, e.g., as indicated on information supplied by the manufacturer. Lower doses are recommended for initial treatment, with increasing dosages as warranted, using as criteria data obtained during the course of maintenance of the implant. Criteria for adjusting dosage can include level of production of the desired biological product of the encapsulated therapeutic substance, for example, production of insulin, production of thyroxin, and the like. When assays indicate diminishment, increases in NSAID dose for further therapeutic regimens are suggested. Functional assay of the cells in the implant, e.g., in the case of islet cells, the ability to secrete insulin in vitro, or to regulate blood glucose, can also be used. The NSAID or mixture of NSAIDs of choice can be administered prior to, at the time of, and/or after implantation of microcapsules or other device; administration can be at regular intervals such as, for time-release and other formulations, monthly, weekly, daily, and for standard formulations, twice or three times daily or other multiple administration schedules.

Dosages can be determined by methods known in the art. Dosages can be started at levels recommended by the manufacturer for NSAIDs such as aspirin, naproxen and acetaminophen; further therapy can be adjusted by increasing or decreasing the dose to achieve optimal effect. For therapy during extended implantation, analysis of active production by the encapsulated biological source can be used to indicate NSAID administration. For example, NSAIDs can be administered, or dosage of NSAID increased, at a time such that a decrease in insulin production has been observed, or at a time that production of insulin falls below a particular threshold. Insulin production as a test of success of microcapsule implantation is exemplary, and is not used here to delimit the methods, but to illustrate one means of adjusting NSAID dose.

NSAIDs can be formulated to have one or more characteristics, including the following: effervescent, flavored, coated, combined with another agent such as codeine, chewable, time-released, tri-buffered, micronized, and enteric coated to resist disintegration in the stomach, dissolving in the more neutral-to-alkaline environment of the duodenum.

Implantable Devices

Any implantable device, e.g., those which include one or more cells encapsulated in a medium, e.g., a shape-retaining gel, can be used with the method of the invention. In most cases these devices will include one or more cells encapsulated in a semipermeable membrane. Commonly they are microcapsules which include one or more cells encapsulated in a shape-retaining gel and an immunoisolating coating which preferably surrounds the shape retaining gel.

A microcapsule typically includes an inner gel, e.g., hydrogel, core in which living cells are embedded and optionally a semipermeable coating enclosing the gel. The coating often has a porosity which prevents components of the implant recipient's immune system from entering and destroying the cells within the microcapsule. Gel microcapsules containing a small number of living cells have been used to transplant both allogeneic and xenogeneic donor cells into recipient animals. Several methods for microencapsulating cells, e.g., pancreatic islet cells, in an alginate gel have been devised. These include the alginate-polylysine technique described in Lim et al., U.S. Pat. No. 4,391,909 and Soon-Shiong et al., *Transplantation*, 54:769–774 (1992), the alginate-chitosan system described in Rha et al., U.S. Pat. No. 4,744,933, and the polyacrylate encapsulation method described in Sefton, U.S. Pat. No. 4,353,888.

A microcapsule should preserve the viability of the encapsulated material, allow rapid, timely and adequate release of donor tissue produced substances, and satisfy other clinical requirements. The microcapsule should possess the following properties:

(1) it should allow relatively efficient diffusion of critical nutrients from the recipient environment into the microcapsule;

(2) it should allow relatively efficient diffusion of donor cell waste products out of the microcapsule;

(3) it should allow efficient diffusion of recipient signal molecules, e.g., in the case of the treatment of diabetes, glucose, into the microcapsule;

(4) it should allow diffusion of the critical substance supplied by the encapsulated cells, e.g., in the case of the treatment of diabetes, insulin, into the recipient milieu;

(5) it should minimize non-immune inactivation, e.g., by fibrotic encapsulation, of the microcapsule;

(6) it should minimize contact of the recipient's immune system with the encapsulated cells;

(7) it should use, to the extent possible, biocompatible materials; and (8) it should be biocompatible with respect to the graft or islet tissue.

Preferably the permeability barrier of the microcapsule has a molecular weight cut-off of about 50 kDa, preferably more than about 100 kDa, preferably more than about 150 kDa, and most preferably more than about 400 kDa. Particularly preferred embodiments the cutoff should be between 50 kDa and 120 kDa. The cut-off can be such that immune system components such as Ig molecules or complement, or recipient-derived cells, are excluded.

The coating (which is optional) can include: a polyamino acid, e.g., polylysine (PLL) or polyornithine (PLO); a naturally occurring substance, e.g., chitosan. A particularly preferred coating is polyamino acid, e.g., polylysine or polyomithine, having a molecular weight of less than 15 kDa, more preferably of less than 10 kDa, more preferably of less than 5 kDa. Particularly preferred are polyarnino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Also preferred are polyaminoacid, e.g., PLL or PLO, coatings in the range of 1 or 2–10 kD, preferably in the range of 1–2, 1–3, or 1–4 kD. In other preferred embodiments, the molecular weight is between 2 and 50,000, more preferably between 3,000 and 30,000.

The diameter of the microcapsule can, by way of example, be between 100 microns and 10 millimeters, between 200 and 800 microns, between 200 and 1800 microns, between 400 and 8,000 microns, or between 400 and 2,000 microns. In preferred embodiments the diameter is about 800 microns. Microcapsules of the invention are preferably less than 8,000, more preferably less than 3,500, 3,000, 2,500, 2,000, 1,500, or 1,000 microns in diameter. In preferred embodiments the microcapsules are preferably more than 80, more preferably more than 200, 400, 600, 800, 1,000, 1,500, 2,000, 3,000, 4,000, or 5,000, 6,000, 7,000, 8,000, or 10,000 (10 mm) microns in diameter.

The microcapsule can be of sufficient diameter, such that it imposes a substantial distance (or separation) between recipient cells, e.g., lymphocytes, macrophages, or NK (natural killer) cells, and the source of a therapeutic substance. In more preferred embodiments the distance between an encapsulated cell and the outer surface of the microcapsule is at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.g., by diffusion), e.g., reduced at least 10, 20, 50, 75, or 90%; sufficient such that the concentration of small molecules (e.g., molecules which are not excluded by the semipermeable barrier-components of the microcapsule, e.g., cytokines, NO, and other toxic moieties) released by recipient cells is substantially reduced (e.g., by diffusion), e.g., reduced at least 10, 20, 50, 75, or 90% at the source of a therapeutic substance.

The microcapsule can be geometrically stabilized. For example, a component of the microcapsule is geometrically stabilized, e.g., by allowing it to age for between 2 hours and 14 days, e.g., for between 12 hours and 4 or 5 days, prior to coating it.

The outer surface of the composite can be biologically compatible, e.g., it is sufficiently smooth that it inhibits fibrotic encapsulation of the composite; the outer surface of the composite is biologically compatible, e.g., it is sufficiently smooth that it inhibit fibrotic encapsulation of the composite but the surface of the internal particle is not biologically compatible, e.g., it is not sufficiently smooth to inhibit fibrotic encapsulation.

Many methods for encapsulating cells are known in the art. A few are discussed below. These are cited merely as examples, and are not the only methods which can be used.

Encapsulation using a water soluble gum to obtain a semi-permeable water insoluble gel to encapsulate cells for production and other methods of encapsulation are disclosed in U.S. Pat. No. 4,352,883 issued Oct. 5, 1992.

U.S. Pat. No. 4,409,331 issued Oct. 11, 1983 discloses a process for production of substances from encapsulated cells, molecular weight cut-off of membranes, use of divalent cations for polymerization, use of various therapeutic substances, core materials, and methods of formation of the gel including cross-linkers.

Shape-retaining gelled masses that expand before membrane formation, and upon contact with chelator can be made to liquify within the membrane, and having an optional second membrane are disclosed in U.S. Pat. No. 4,663,286 which issued May 5, 1987.

Double-membrane capsules with high molecular weight cut-offs such as 200–400 kD for the inner membrane, enabling higher density growth of encapsulated cells, and use of poly-L-lys, are disclosed in EPO Publ. No. 0301 777 of Jan. 2, 1989.

U.S. Pat. No. 5,084,350 issued Jan. 28, 1992, discloses gels reliquified within the capsule for a variety of biological samples, and materials for other microcapsule components.

U.S. Pat. No. 5,427,935 issued Jun. 27, 1995, discloses composite hybrid membranes of compositions that include chitosan.

Microcapsules with multiple coatings including a halo layer, and not requiring a poly-L-lysine or other polyamino acid or polycation coating are disclosed in WO 95/19743 published Jul. 27, 1995.

Macrocapsular surfaces of decreased surface area and roughness and increased cryoprotectivity, with a variety of co-monomers and free radical initiators of polymerization, are disclosed in U.S. Pat. No. 5,545,423 which issued Aug. 13, 1996.

Methods of the invention can be used with any implantable device which is suitable for delivery and maintenance of biologically active material. Particularly preferred devices include gel-based microcapsules, for example, the composite microcapsules described herein and in U.S. Pat. No. 5,427,935 (Jun. 27, 1995). However, other devices can be used as well, for example, the devices described in U.S. Pat. No. 4,663,286 (May 5, 1987), particularly, the implantable devices described in U.S. Pat. No. 5,545,423 (Aug. 13, 1996).

Sources of therapeutic substances

Implantable devices used in methods of the invention will generally include a source of a therapeutic substance, e.g., a cell or tissue.

Preferably the source will be one or more living cells. Cells can be growth-inhibited, such that they do not divide, but continue to perform metabolic reactions. Growth inhibition can be achieved by one or more methods known to one with skill in the art, such as irradiation with UV light, by treatment with mitomycin, and by appropriate genetic manipulation. Exemplary cells include pancreatic islets, hepatic cells, neural cells, liver cells, renal cortex cells, vascular endothelial cells, thyroid and parathyroid cells, thymic cells, ovarian cells, blood cells, allografts or xenografts, and genetically engineered cells. Sources of cells and tissues containing cells include, without limitation, tissue or cells removed from a donor animal, tissue or cells of a primary cell culture obtained by incubation or cultivation of donor tissues and cells, cells obtained from viable cell lines and immortalized cell lines, biologically active products of cells or tissues, and the like. Cells from a primary cell line can be treated in culture with one or more cytokines or growth factors. Exemplary cells for transplantation into a subject can be from the same species as that subject, or from a different species that is discordant or concordant with the recipient subject.

In preferred embodiments the cell is an autologous cell, an allogeneic cell, or a xenogeneic cell. For example, the cell is: an autologous cell, i.e., a cell which is taken from the individual recipient into which the cell will be implanted; an allogeneic cell, i.e., a cell which is taken from a different individual of the same species as the recipient into which the cell will be implanted; a xenogeneic cell, i.e., a cell which is from a different species than the recipient into which the cell will be implanted. In the case of an allogeneic cell, the cell can be fully matched or partially matched for MHC class I loci, fully matched or partially matched for MHC class II loci, and fully matched or partially matched for minor loci. In the case of xenogeneic cells, the cells can be concordant or discordant with respect to the recipient.

In preferred embodiments the recipient animal is a dog, a pig, or a human. In preferred embodiments the donor cell is a pancreatic islet cell. In preferred embodiments: the composite microcapsule contains pancreatic islets, e.g., at e.g., a density of 5,000 to 100,000 islets per milliliter of medium; the composite microcapsule contains living cells at a density of about $10^5$ to $10^8$ cells per milliliter of medium.

Implantable devices used in the methods described herein can include a source of a therapeutic substance. For example, the device can include, a composition of matter which produces or releases a therapeutic substance, e.g., a protein, e.g., an enzyme, hormone, antibody, or cytokine, a sense or anti-sense nucleic acid, e.g., DNA or RNA, or other substance which can exert a desired effect on a recipient. The source of a therapeutic substance can be a tissue or a living cell; a eukaryotic cell, e.g., a rodent, canine, porcine, or human cell; a prokaryotic cell, e.g., a bacterial cell; a fungal or plant cell; a cell which is genetically engineered, e.g., a cell which is genetically engineered to produce a protein, e.g., a human protein. The source of a therapeutic substance can be or include an autologous, an allogeneic, or a xenogeneic cell. For example, the cell is: an autologous cell, i.e., a cell which is taken from the individual recipient into which the cell will be implanted; an allogeneic cell, i.e., a cell which is taken from a different individual of the same species as the recipient into which the cell will be implanted; a xenogeneic cell, i.e., a cell which is from a different species than the recipient into which the cell will be implanted. In the case of an allogeneic cell, the cell can be fully matched or partially matched for MHC class I loci, fully matched or partially matched for MHC class II loci, and fully matched or partially matched for minor loci. In this case of xenogeneic cells, the cells can be concordant or discordant with respect to the recipient.

Implantable devices used in the methods described herein can include a composition of matter which absorbs or modifies or detoxifies a substance produced by the recipient.

Genetically modified cells can be used. This includes cells that have been modified by genetic engineering to produce a product, e.g., cells modified to overproduce a product they normally produce, as well as cells engineered to produce a produce they do not normally make. Cells which have been modified in other ways, e.g., cells modified to reduce an immune response in a subject, can also be used in methods of the invention.

Gel microcapsules

As described elsewhere herein, gel-based microcapsules are particularly preferred for use in the methods of the invention. Gel-based microcapsules usually include a source of therapeutic substance, a gel-core enclosing the source, and often an immuno-isolating layer.

Exemplary materials for the gel-core include, agaroses, alginates, alginate preparations containing high guluronic acid levels, polyethylene glycol (PEG; also called polyethylene oxide, PEO) preparation of varying molecular weights and synthetic gels. Alginates as described in U.S. Pat. No. 5,545,423 are particularly preferred.

Exemplary materials for the immuno-isolating layer include polymers, e.g., charged polymers, preferably positively charged polymers, e.g., poly-amino acids, synthetic polypeptides, or polymers of substituents with free amino groups, such as poly-L-lysine (PLL), polyarginine, and polyornithine. Also included are co-polymer and heteropolymer mixtures of amino-containing monomer subunits.

Isolation of Cells
Production of Encapsulated Cells

Living cells can be isolated away from surrounding tissues or grown in culture by procedures known to the art, and then suspended in a liquid medium prior to encapsulation. The living cells can provide biological substances, e.g., enzymes or co-factors, hormones, clotting factors, or growth factors. Cells, e.g., pancreatic cells, can provide enzymatic or hormonal functions. Cells such as hepatic cells can provide a detoxification function.

As an example, pancreatic islet cells were prepared from either adult mongrel dogs, pigs, or bovine calves (0–2 weeks old) by a modification of the methods of Warnock and Rajotte, *Diabetes*, 37:467 (1988), as previously described in Lanza et al., *Proc. Natl. Acad. Sci.*, 88:11100–11104 (1991).

Briefly, aseptic, viable porcine pancreata were obtained under aseptic operating room procedures. After resection (warm ischemia for less than about 15 minutes), the glands were cannulated and infused with cold (4° C.) University of Wisconsin (UW) organ preservation solution. Pancreatic tissues were dissociated using an intraductal collagenase digestion procedure. The collagenase is delivered by peristaltic pump, and the digested pancreas is mechanically disrupted in a polypropylene dissociation chamber containing 2–6 mm glass beads. The islets were separated from the exocrine tissue by discontinuous density gradient centrifugation (27%, 20.5%, and 11% (w/v) FICOLL® (Sigma, F 9378) in Eurocollins solution).

Isolated islets were then cultured for one day either in M199/Earle's medium supplemented with 10% (vol/vol) fetal bovine serum, 30 mM HEPES, 100 milligrams/dl glucose, and 400 IU/ml penicillin (canine), or in α-MEM plus 10% heat-inactivated horse serum (bovine and porcine) in a humidified atmosphere of 5% $CO_2$/95% air at 37° C. A typical yield of islets should be in the range of 0.5–1.8×$10^6$ islets for adult pancreas (400 gm wet weight, islet diameter 80–125 μm, purity 85–95%, viability greater than 90%; see below). The cells can also be isolated by other procedures and cultured under other suitable conditions.

Ischemic deterioration of the islet cells is minimized by using tissue fragments of a suitable size, e.g., islet fragments should be less than about 150 microns, and preferably 50 to 125 microns, in diameter. Viability, growth, longevity, and/or function of the islet cells can be enhanced by co-culturing, i.e., by mixing other cell types in the liquid medium prior to encapsulation. Useful cell types include cells which secrete growth hormone, e.g., GH-3 cells, or cells which secrete connective tissue and/or extracellular matrix components, e.g., fibroblasts and endothelial cells. In addition, cells, e.g., islets, can be co-cultured with red blood cells, or hemoglobin, or other oxygen carrying agents can be added, to enhance oxygen availability. Red blood cells can also be used to scavenge nitrous oxide.

Islet quality control procedures are used to enable comparison of different lots of islets prepared at different times. Purity (amount of islet tissue compared to exocrine tissue contamination) can be determined by ability of pancreatic islets to rapidly take up diphenyl thiocarbazone (dithizone). Islets can be incubated for five to ten minutes with 50 micrograms/ml of dithizone (D5130, Sigma) to stain them red. The preparation is then examined under light microscopy for a qualitative estimate of purity. Quantification of purity is effected by islet dispersion and counting of stained and unstained cells, or with a spectrophotometric assay of dithizone uptake/micrograms DNA.

Viability can be determined by any one of several assays that depend on the capability of viable cells to exclude certain dyes. For example, one assay uses a combination of the fluorescent stains acridine orange, which stains only viable cells green, and propidium iodide, which stains only the nuclei of dead cells red. The islets are incubated with the dyes (acridine orange, Sigma A6014, 50 micrograms/ml, and propidium iodide, Sigma P4170, 2.5 micrograms/ml) in a PBS solution for 10 to 15 minutes and then dispersed into single cells. Counts of red and green fluorescing cells are used to calculate percent viability.

Insulin secretory activity of the islets is determined both in static culture, e.g., expressed as units of insulin per islet volume, and based on the capability of the islets to respond to graded concentrations of glucose. These values are quantitatively established by measuring the insulin secreted by islets exposed to a range of glucose concentrations extending from 2.8 to 28 milliM glucose.

Formation of Microcapsules

Living cells, e.g., islet cells, can be encapsulated in a variety of gels, e.g., alginate, to form microparticles, e.g., microbeads or microspheres to physically isolate the cells once implanted into a host. To prevent entry of smaller molecular weight substances such as antibodies and complement (with a molecular weight of about 150 kDa) into these microparticles, they can be coated with a material such as poly-L-lysine, chitosan, or PAN-PVC, which provides an outer shell with a controlled pore size, or they can be treated by, e.g., cross-linking, to control their internal porosity. Alternatively, their porosity can be controlled by mixing various substances such as polyethylene oxide (PEO) directly into the gel mixture. The use of a high molecular weight molecule, e.g., a high molecular weight PEO, e.g., of about 1–8 million Da, will minimize the escape of the porosity controlling substance. Molecules of this size range can be used with or without an outer coating.

Encapsulation

Once the cells are isolated and suspended in liquid medium, they can be encapsulated by a supporting matrix, e.g., a hydrogel matrix to form a microbead, which serves as a core of a microcapsule, e.g., or internal particle. The core maintains a proper cell distribution, provides strength, and enhances cell viability, longevity, and function. The core can also contribute to immunoisolation. For example, the physical distance that is created by embedding the internal particle in a supporting matrix, can provide protection from, e.g., nitric oxide and cytokines. It also protects the internal particle from direct cell-cell interactions that can elicit an undesirable host response.

Using standard techniques, a gel matrix is formed by adding cells, e.g., pancreatic islets, to a solution of nutrient medium and liquefied gel, e.g., sodium alginate, to form a suspension, and then crosslinking the gel. The gel matrix can be any one or a combination of a variety of substances, preferably substances that are biocompatible with the host animal, and are capable of maintaining cellular viability and physically supporting the tissue or cells in suspension.

The gels can be gelled or crosslinked, e.g., by the addition of ions such as calcium, potassium, or barium, or by a change in temperature. If temperature change is used, however, care should be taken to choose appropriate temperature changes for gelation that are not harmful or fatal to the living cells to be encapsulated. Temperature-independent gels include alginates, carrageenans, and gums such as xanthan gum. As used herein, the term alginate includes alginate derivatives. These gels should be treated using standard techniques, to remove polyphenols, lipopolysaccharides, endotoxins, and other impurities.

Alginate is composed of blocks of 1,4 linked β-D-mannuronic acid (M) and α-1-guluronic acid (G) linked together, e.g., in alternating MG blocks. The preferred alginate is one formulated with a high G block content, e.g., at least about 60 percent. The higher the percentage of G blocks in the alginate composition, the greater the pore size and the strength of the gel matrix that is obtained in the final product. In addition, alginate gels with a high M block content appear to be more immunogenic than gels with a high G block content. See, e.g., Soon-Shiong et al., *Transplant. Proc.*, 23:758–759 (1991), and Soon-Shiong et al., *Transplantation*, 54:769–774 (1992).

The gel matrix should be sufficiently viscous to maintain the cells in a dispersed state. When alginate is used as the gel matrix, it is added up to about 3%, preferably to about 1 to 2%, of the liquid medium, and the solution is cross-linked to form a semisolid gel in which the cells are suspended. These percentages provide a matrix that maintains its shape and has sufficient mechanical strength to remain intact in vivo for several months.

Alginate hydrogels are preferred for the microbead cores for a number of reasons. Alginate allows rapid polymerization and immobilization of cells at room temperature using relatively benign $CaCl_2$, provides consistent gel rheology that can be conveniently varied by increasing alginate concentration, and produces microbeads with good mechanical strength.

A preferred method for making hydrogel microbeads is with an air jet.

Other methods for making hydrogel microbeads including emulsification, dripping, and the Rayleigh jet.

Emulsification

Emulsification depends upon shear forces in an immiscible liquid to break up the pre-gel liquid. The shear forces are usually produced by agitation although they can be produced by wall shear in a lumen or by sonification. Well controlled agitation can produce droplets which are uniform to about ±15% in diameter, and it is an acceptable technique often used to encapsulate living cells. See, e.g., Lencki et al., U.S. Pat. No. 4,822,534.

Dripping

In this group of related techniques, a force is applied to pre-gel liquid in which living cells are suspended, which overcomes the surface tension force between the forming droplet and the extruding orifice. The orifice can take many forms; frequently a blunt-tipped hypodermic needle is used.

Various forces can be applied to the droplets, e.g., centrifugal, electrostatic, or inertial. A centrifugal force of about 536 g is suitable for use with an extrusion orifice large enough to pass 100 μm islets to produce 200 μm droplets. A suitable rotor to produce microspheres with centrifugal force is a multiorifice centrifugal head, e.g., as described in Deasy (ed.), "Microencapsulation and Related Drug Processes," Chapter 13 (Marcel Dekker, Inc., NY & Basel, 1984) (Southwest Research Institute, San Antonio, Tx.). Another suitable rotor is described in U.S. Pat. No. 4,386,895.

Axial inertial forces, as employed in ink jets which "spit" a single droplet from an orifice by pulsing a pumping chamber with a piezoelectric crystal, or in so-called "bubble" jets which boil microvolumes of fluid to create a pressure pulse, are also suitable for the present invention.

Fluid flow drag is another common method used to form microdroplets in the 200 to 1000 µm size range. In this method, a liquid is extruded steadily from an orifice (usually a hypodermic needle) which is arranged within a coaxial jet of gas. The drag force "shear" of the gas flow, with a velocity of up to 400 m/sec, pulls the forming droplet away from the needle against the retaining force of surface tension. The droplets are typically twice the diameter of the orifice, which makes 400 µm diameter droplets, with less than or equal to 100 µm diameter islets, the smallest practical size using this method.

Rayleigh Jet

The Rayleigh jet can be used to manufacture very uniform (±1%) microdroplets and even encapsulated microdroplets by means of two coaxial jets. This technique is based upon the principle, first illustrated by Lord Rayleigh in 1873, that a liquid jet is inherently unstable against surface tension. Rayleigh demonstrated that there is a particular geometry that produces a characteristic frequency (where f=frequency; V=jet velocity, D=diameter of microdroplet): f=0.419 V/D.

Although the drop-passing frequency is completely determined by the jet velocity, the droplet-forming process is completely independent of the jet velocity. This phenomenon has been used to manufacture microdroplets from 20 µm to 1000 µm diameter from liquids ranging in viscosity from 1 to 100,000 cps. The jet is disturbed at the Rayleigh frequency by either natural turbulence or, usually, by driving the plenum supplying the jet with an oscillator, typically a piezoelectric crystal, or by inertial forces arising from vibrating the nozzle transversely or axially. Electrostatic or acoustic excitation of the jet can also be employed.

By employing a coaxial flow of an encapsulating liquid and a coating liquid, coated droplets can be formed. Coextrusion is very attractive as long as the core material does not cause a rapid coagulation of the shell material. When the droplets are to be coated with a rapidly coagulating material such as an acrylic copolymer, a temporary barrier liquid (e.g., vegetable oil or a polymer solvent) should be interposed between the core and coating materials.

Controlling Pore Size of Microparticles

The pore size of the microparticles can be controlled either by applying a semipermeable shell having a particular molecular weight cutoff. This can be effected by applying an "electrostatic" coating, e.g., a coating of a polyamino acid, e.g., polylysine. Pore size can also be controlled by treating the gel matrix of the microparticles themselves to change the pore size of the matrix without any subsequent coating. E.g., the surface of the core can be altered by, e.g., cross-linking, to produce covalently modified gel matrix surface. A coating can be a formed by modifying the structure of the matrix, e.g., the matrix can be cross-linked, e.g., with metal ions, e.g., Ba or Fe ions, or by photo-cross-linking, to form an coating.

As used herein, "molecular weight cutoff" refers to the size of the largest molecule that is not substantially blocked, e.g., by a semipermeable shell or coating surrounding a microsphere or by the gel matrix itself or both. Molecules with a molecular weight above the cutoff are substantially prevented from entering or leaving the particle. The composite microcapsule should generally provide a molecular weight cutoff of about 50,000, more preferably about 100,000, more preferably about 150,000, and most preferably about 400,000 daltons. In preferred embodiments, the molecular weight cutoff is sufficient to prevent Ig molecules, e. g., IgG, and complement, from entering and coming into contact with the encapsulated material.

Altering the Pore Size of the Gel Matrix

The pore size of the gel matrix can be altered in several ways. For example, the gel matrix can be altered, e.g., the porosity can be either increased or decreased so as to influence the transport properties, e.g., permeability and/or molecular weight cutoff, by adding, e.g., gelatin, or collagen, or barium, or other ions with the same valance as $Ca^{++}$ ions. Changes in the temperature will also affect the pore size.

An increase in the temperature will result in shrinkage of the gel matrix. The addition of compound, e.g., PEO, to the gel matrix can also result in altered pore size. PLO can act to repel protein and to hinder fibrotic response. In preferred embodiments, PEO of molecular weight greater than 1,000,000 Da, more preferably greater than 4,000,000 Da, and most preferably greater than 8,000,000 Da, is mixed with the gel matrix. PEO of relatively high molecular weight will not diffuse out and thus does not require crosslinking.

Coating with Polylysine

To coat an alginate core with polylysine the alginate core is dropped into a solution of 0.05% polylysine in serum free culture medium. The thickness of the polylysine coating can be increased by increasing the time the alginate core is left in the solution, or alternatively, by increasing the concentration of the solution. The volume of beads to solution can be, e.g., 1:5, 1:10, or 1:20. For smaller beads a greater proportion of solution is desirable.

Coatings which minimize particle volume

Embodiments of the invention use coatings which reduce the volume of a component, e.g., a core, to which they are applied. For example, a polyaminoacid coating, e.g., a polylysine, or polyornithine made from a polyaminoacid of a relatively low molecular weight, can result in a significant reduction in the volume of a gel core, e.g., an alginate core, to which it is applied. In many cases the reduction in volume is as much as about 50%, or even 60–70%, or more.

Relatively low molecular weight, as used herein, means about 30,000 Da or less, more preferably about 15,000 Da or less, more preferably about 10,000 Da or less, more preferably about 8,000 Da or less, more preferably about 7,000 Da or less, more preferably about 5,000 Da or less, more preferably about 4,000 Da or less, more preferably about 3,000 Da or less, and most preferably about 1,500 Da or less.

For example, the use of polylysine of a relatively low molecular weight, e.g., 3, 7, or 9.6 kDa, can result in a significant reduction, (approximately 30% in some cases) in the diameter, of the core to which it is applied. In addition to the decrease in volume, the use of a low molecular weight polyamino acid will result in a coat having superior permselective properties. However, the use of a low molecular weight polyaminoacid often results in a surface which is "pruned", i.e., relatively convoluted or rough, and which can elicit a fibrotic response. The composite microcapsule of the invention, by using this coating on the internal particle, and a smooth surface, e.g., of alginate, on the exterior of the composite microcapsule, can obtain the benefits of a coating of relatively low molecular weight and also inhibit fibrosis.

The permselectivity properties of a poly amino acid, e.g., a polylysine, coating improve after the coating has been aged 2 or more hours. Thus, for best results, particles coated with these coatings should not be implanted in recipients until the coating has aged.

Geometric Stabilization

Some particles or components are not geometrically stable immediately after manufacture, e.g., the particle or component can change size or shape. If internal particles which are incorporated into a composite microcapsule change geometry, the components of the composite microcapsule, e.g., the super matrix or outer coating, can be damaged and the integrity of the composite microcapsule can be compromised. Although not wishing to be bound by theory, the inventors believe that changes in the geometry can damage the super matrix or the outer coating, e.g., by inducing fissures or discontinuities. Damaged particles can allow the fibrotic proliferation of recipient cells on the inner particles when implanted into a recipient. Therefore, it is often desirable to geometrically stabilize internal particles, preferably prior to incorporating them into composite microcapsules. Stabilization can generally be accomplished by allowing the particles to "age" for a short time before incorporation into larger structures. The aging should be done under condition which maximizes the viability of encapsulated cells. Geometric stabilization is particularly important when the particles are coated with a relatively low molecular weight poly-amino acid.

Polylysine-coated alginate particles, especially those coated with relatively low molecular weight polylysine, should be geometrically stabilized. The polylysine coated alginate particles should be placed in a culture medium, suitable for the cell being used, and allowed to stabilize overnight.

Formation of Composite microcapsules

Composite microcapsules, e.g., those described in PCT/US96/03135 can be used in the invention.

Implantation

The microcapsules can be implanted into a host by injection with a standard catheter or syringe, e.g., with a 16 gauge needle for beads less than 1000 μm in diameter. Larger microcapsules can be inserted via a small incision, e.g., with a catheter or funnel-like device. The beads are preferably implanted into the host intraperitoneally. The beads can also be implanted intramuscularly or subcutaneously. Alternatively, the beads can also be implanted into immunoprivileged sites such as the brain, testes, or thymus, where the host's immune response is least vigorous, as described in Chapter 7 of Lanza et al. (eds.), *Immunomodulation of pancreatic Islets* (RG Landes, Tx., 1994). Composite microcapsules can also be introduced at a site where the substance provided by the composite microcapsule is needed locally. E.g., a microcapsule which provides α-interferon could be implanted in tumors. The microcapsules of the invention can be delivered to a subcutaneous site. The composite microcapsules can be inserted through a small surgically created opening using a gun/trocar type device that slips the beads under the skin.

A suitable host for the invention can be a subject or a patient. The term "subject," as used herein, refers to a living animal or human in need of therapy for, or susceptible to, a condition, which is remediable through microcapsular implantation. In preferred embodiments, the subject is a mammal, including humans and non-human mammals such as dogs, cats, pigs, cows, sheep, goats, horses, rats, and mice. In the most preferred embodiment, the subject is a human. The term "subject" does not preclude individuals that are normal in all respects. The subject can formerly have been treated surgically or by chemotherapy, and can be under treatment by microcapsular implantation, and can have been so treated in the past.

The term "patient," as used herein, refers to a human subject who has presented at a clinical setting with a particular symptom or symptoms suggesting treatment by implantation of microcapsules. A patient's diagnosis can alter during the course of disease progression, such as development of further disease symptoms, or remission of the disease, either spontaneously or during the course of a therapeutic regimen or treatment.

Pharmaceutical Compositions

The compounds of the invention include NSAIDs that have been formulated for oral administration. The Examples below are not intended as delimiting with respect to the nature of the NSAID, or to a particular route of the administration and additional routes are listed herein, infra. In another embodiment of the present invention, the NSAIDs can be administered by combination therapy, i.e., combined with other agents. For example, the combination therapy can include a composition of the present invention with at least one other NSAID, at least one antibiotic, or other conventional therapy.

As used herein, "pharmaceutically acceptable carrier" includes any and all solvents, dispersion media, coatings, antibacterial and antifungal agents, isotonic and absorption delaying agents, and the like that are physiologically compatible. The use of such media and agents for pharmaceutically active substances is well known in the art. Preferably, the carrier is suitable for oral, intravenous, intramuscular, subcutaneous, parenteral, spinal or epidermal administration (e.g., by injection or infusion). Depending on the route of administration, the active compound can be coated in a material to protect the compound from the action of acids and other natural conditions that can inactivate the compound.

The phrases "parenteral administration" and "administered parenterally" as used herein means modes of administration other than oral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation.

Transdermal patches offer the advantage of providing controlled delivery of a compound of the present therapeutic inventions to the body. Absorption enhancers can also be used to increase the flux of the composition across the skin. The rate of such flux can be controlled by either providing a rate controlling membrane or dispersing the composition in a polymer matrix or gel. Devices, including patches, which transdermally deliver a composition by iontophoresis or other electrically-assisted methods can also be employed in the present invention, including, for example, the devices described in U.S. Pat. Nos. 4,708,716 and 5,372,579.

One of ordinary skill in the art can determine and prescribe the effective amount of the pharmaceutical composition required. For example, one could start doses of the known or novel NSAID levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous. If administered proximal to the site of the target site of device implantation, then delivery routes other than oral and intravenous delivery are preferred. If desired, the effective daily dose of a therapeutic compositions can be administered as two, three, four, five, six or more sub-doses administered separately at appropriate intervals throughout the day, optionally, in unit dosage forms.

Methods of the invention reduce or eliminate the need for immunosuppression in a recipient subject. In some instances, limited administration of immunosuppressive agents can be desirable. Immunosuppressive treatment can include: administering to the recipient adjunctive immunosuppression for less than one year, 180 days, 90 days, 60 days, or 30 days; administering a drug to the host animal at a dosage effective to inhibit fibrosis and inflammation around the uncoated particle, but at a dosage lower than that required to achieve the same effect when an NSAID is not used. For example, cyclosporin A can be administered at a dosage that achieves a whole blood trough level of less than about 100 ng/ml in the host animal.

EXAMPLES

The invention is further illustrated by the following examples, which should not be construed as further limiting. The contents of all references, pending patent applications and published patents, cited throughout this application, are hereby expressly incorporated by reference.

Example 1

Fibrosis of Microcapsules Implanted in the Peritoneum of Dogs, and Cyclosporin A Suppression of Fibrosis Composite microcapsules (alginate-polylysine) containing discordant bovine and porcine islets were tested in normal adult mongrel dogs. In a series of experiments, encapsulated bovine islets were implanted into the peritoneum for periods of 2 weeks to two months, as indicated for each animal in Table 1. The islet tissue remained viable both with and without low-dose CsA immunosuppression (CsA was provided at 10 milligrams/kg/day). Immunohistochemical staining revealed well-granulated alpha, beta, and delta cells consistent with functionally active hormone synthesis and secretion.

The number of observed nonfibrosed "free-floating" microcapsules recovered from the peritoneum of the non-immunosuppressed control animals was considerably lower than that recovered from animals that had been administered CsA therapy.

Example 2

Effect of Nonsteroidal Anti-inflammatory Agent (NSAID) Therapy on Fibrosis

Composite microcapsules (alginate-polylysine) containing discordant bovine and porcine islets were tested in normal adult mongrel dogs. In a series of experiments, encapsulated bovine or porcine islets were implanted into the peritoneum for periods of two weeks to two months, as indicated in Table 1. Seven dogs were used to test the effects of nonsteroidal anti-inflammatory agent therapy: aspirin (350 milligrams b.i.d) and naproxen (5 milligrams/kg/day) were administered to two of the animals. Naproxen (5 mg/kg/day) was administered to five dogs. Control animals received no additional immunosuppressive or anti-inflammatory agents. The dogs were sacrificed and microcapsules spheres were examined for appearance of fibrosis. The results of these studies are summarized in Table 1 below.

The external surfaces of the implanted spheres in the naproxen and aspirin/naproxen-treated dog were free of fibrosis and host cell adherence, whereas the majority of the spheres in the untreated animals were encapsulated by thick layers of organized granulation tissue.

The data in Table 1 show that naproxen (Aleve, an over-the-counter medicine) alone is sufficient to eliminate the fibrotic response elicited by the microcapsules. In addition, the appearance of spheres taken from dogs 8 and 9 support a model in which aspirin is competing with naproxen for the same cell target receptor, thus reducing somewhat the efficacy of the naproxen.

TABLE 1

Effect of NSAIDs on fibrosis of microcapsules implanted into the peritoneal cavity of normal dogs for 1 month

| | | | | Amount and Appearance of Spheres | |
| --- | --- | --- | --- | --- | --- |
| Dog | Drug | Source of Islets | Time | Non-fibrotic | Fibrotic |
| 1 | none | porcine | 1 month | few | moderate |
| 2 | none | porcine | 1 month | none | no spheres |
| 3 | none | porcine | 1 month | few | severe |
| 4 | none | bovine | 1 month | few | moderate |
| 5 | none | bovine | 1 month | few | moderate |
| 6 | none | bovine | 1 month | few | moderate |
| 7 | none | bovine | 1 month | few | severe |
| 8 | nap/asp[2] | bovine | 1 month | most | none |
| 9 | nap/asp | porcine | 1 month | most (70–80%) | little-to none |
| 10 | nap alone | porcine | 1 month | all (99%) | none |
| 11 | nap alone | porcine | 2 weeks | all | none |
| 12 | nap alone | porcine | 2 weeks | all | none |
| 13 | nap alone | porcine | 2 months | all | little-to-none |
| 14 | nap alone | porcine | 2 months | all | none | nap/asp = naproxen (5 milligrams/kg/day) and aspirin (350 milligrams/kg/b.i.d)

Other Embodiments

NSAID-related methods of the invention can be used to treat a variety of disorders. These include disorders that result from the defective or insufficient production of a particular substance, e.g., enzyme or hormone, and other disorders, e.g., trauma-related disorders, such as spinal cord injury.

A number of well-characterized disorders caused by the loss or malfunction of specific cells in the body are amenable to microcapsule-medicated replacement therapy. For example, in addition to the islets of Langerhans, which can be used for the treatment of diabetes as described above, hepatocytes can be used for the treatment of hepatic failure, adrenal gland cells can be used for the treatment of Parkinson's disease, nerve growth factor (NGF)-producing cells can be used for the treatment of Alzheimer's disease, factors VIII- and IX-producing cells can be used for the treatment of hemophilia, and endocrine cells can be used for the treatment of disorders resulting from hormone deficiency, e.g., hypoparathyroidism.

Moreover, by using recombinant DNA methods to supply a cell which produces a disease product, or encapsulating other tissues, microcapsules can be used to treat patients suffering from chronic pain, cancer (e.g., hairy cell leukemia, melanoma, and renal carcinoma), AIDS (treated by immunological augmentation), Kaposi's Sarcoma (treated by administration of interferon, IL-2, or TNF-α), primary hematologic disorders, patients with long-lasting aplasia, and patients who are myelosuppressed (treated by bone marrow transplantation and aggressive chemotherapy). Microcapsules should also be useful in the treatment of affective disorders, e.g., Huntington's Disease, Duchenne's Muscular Dystrophy, epilepsy, infertility. Microcapsules can also be used to promote wound healing and to treat traumatic, mechanical, chemical, or thermal injuries, e.g., spinal cord injuries, and in wound healing.

Implantation of specific cells can also serve to detoxify, modify, or remove substances from the circulation, e.g., drugs, poisons, or toxins. For example, the implantation of appropriate living cells restores normal physiologic function by providing replacement for the diseased cells, tissues, or organs, e.g., in hepatic encephalopathy (produced by liver disease) or uremia (produced by kidney failure).

In embodiments of the invention, the encapsulated cells can release fairly large molecules, e.g., IgG molecules. In many applications the critical host component which must be excluded is C1q, which has a molecular weight of about 410 kDa. Thus, the molecular weight cutoff will be about 400 kDa and molecules of up to this size can be released. Genetically engineered cells can also be used in the methods of the invention. For example, cells can be engineered to release larger products, e.g., IgG.

In each application, a sufficient number of composite microcapsules, containing the desired living cells, can be implanted into the patient, e.g., surgically or with a syringe. The microcapsules are implanted, e.g., intraperitoneally, for a systemic effect, or into a particular location, e.g., the brain to treat Parkinson's disease, or the spinal cord to chronic pain or treat spinal cord injuries, for a local effect.

The dose of microcapsules to be used is determined initially from results of in vitro studies. In addition, in vivo results in, e.g., mice, rats, or dogs will facilitate more accurate assessment of required doses, as these tests are generally predictive of efficacy in human patients. For example, canine insulin dependent diabetes represents an excellent model of cellular and humoral autoimmunity (Nelson, *Diabetes Spectrum* 5:324–371 (1992))

The microcapsules are intended to remain in the patient with viable donor cells for extended periods of time up to several months or years. However, if it is determined that the donor cells are no longer viable, e.g., by monitoring the patient's blood for a certain level of the protein secreted by the donor cells, it is a simple task to remove the microcapsules and renew the supply of beads in the patient.

Diabetes Mellitus

To treat diabetes, e.g., in a dog or human patient, the implantable beads preferably encapsulate isolated canine or porcine islets or other cells that produce insulin or insulin-like growth factor 1 (IGF-1). Islets are prepared and encapsulated using procedures described above. Insulin secretory activity of the encapsulated cells or islets is determined both in static culture, e.g., expressed per islet volume, and based on the capability of the islets to respond to graded concentrations of glucose. These values are established as described above. Once the insulin secretion activity of a particular batch of encapsulated islets is determined, the proper number of beads can be determined and implanted into a diabetic patient. For example, to treat a human patient that requires 20 to 50 units of insulin per day, the total number of beads should be selected to contain a total of about 1.0 to 2.5 million porcine islets. For beads designed to contain, on average, 30,000 islets/ml of gel, the proper dosage would be beads made from 30 to 85 ml of gel.

Hemophilia

Hemophilia is an X-linked hereditary bleeding disorder caused by Factor VIII or Factor IX deficiency. Recombinant methods have now been successfully used to create Factor VIII- and Factor IX-producing cells as described above. Encapsulation in microcapsules and implantation of such cells according to the present invention can thus be used for an improved treatment for hemophilia.

Hepatic Diseases

Hepatocyte transplantation is useful not only for irreversible hepatic failure, but for several disease processes including hereditary enzyme abnormalities, acute hepatic failure, where the ability of the liver to regenerate can occur, and as a bridge to whole liver transplantation in patients who develop sudden hepatic failure, either because of medical progression or because of rejection-related complications.

Wong and Chang, *Biomat. Art. Cells Art. Org.*, 16:731 (1988), have demonstrated the viability and regeneration of microencapsulated rat hepatocytes implanted into mice. Viable hepatocytes were microencapsulated in alginate-poly-(L-lysine) and implanted intraperitoneally into normal and galactosamine-induced liver failure mice. Eight days after implantation in the mice with induced liver failure, the viability of the encapsulated rat hepatocytes increased from 42% to nearly 100%. After 29 days, the viability of the encapsulated hepatocytes implanted in normal mice also increased from 42% to nearly 100%. By contrast, free rat hepatocytes implanted into mice all died within four or five days after xenotransplantation. Microcapsules are well-suited to treat hepatic failure.

Other investigators have shown that microencapsulated hepatocytes continue the synthesis and secretion of many specific proteins and enzymes. Cai et al., *Hepatology*, 10:855 (1989), developed and evaluated a system of microencapsulation of primary rat hepatocytes. Urea formation, prothrombin and cholinesterase activity, the incorporation of tritiated leucine into intracellular proteins, and the immunolocation of synthesized albumin were monitored in culture. Despite gradual decreases in some of these activities, the encapsulated hepatocytes continued to function throughout the 35-day observation period. In addition, Bruni and Chang, *Biomat. Art. Cells Art. Org.*, 17:403 (1989),demonstrated the use of microencapsulated hepatocytes to lower bilirubin levels in hyperbilirubinemia. Microencapsulated hepatocytes were injected into the peritoneal cavity of Grunn rats. Bilirubin dropped from 14 milligrams/100 ml to 6 milligrams/100 ml, and remained depressed after 90 days. Again, microcapsules can be used as described above to treat these hepatic diseases.

Parkinson's Disease

Parkinson's disease is a neuronal system disease, involving a degeneration of the nigrostriatal dopaminergic system. Experimental work in both rodents and nonhuman primates has shown that transplantation of fetal tissue containing substantia nigra (dopaminergic) neurons from ventral mesencephalon to dopamine-depleted striatum reinstates near-normal dopamine interinnervation and reduces motor abnormalities. In addition, implantation of adrenal chromaffin cells has been shown to reverse chemically-induced Parkinson's disease in rodents.

Widner et al., *Transplant. Proc.*, 23:793 (1991), reported evidence of fetal nigral allograft survival and function up to 10 months after transplantation and immunosuppression (cyclosporin, azathioprine, and prednisone) in a human Parkinson's patient. Beginning from the second month after the transplantation, they observed a progressive decrease in limb rigidity, increased movement speed in a number of arm, hand, and foot movements, and prolonged "on" periods (greater than 80% increase) after a single dose of L-dopa.

Thus, transplantation of fetal neural tissue, or cells genetically engineered to produce dopamine and nerve growth factors or other neurotropic factors, should have a great potential as a new therapeutic approach in patients with neurological disorders. However, in the case of transplanted xenogeneic donor tissue, rejection would pose a serious problem, even by the combined approach of using an immunoprivileged site and by employing immunosuppressive drugs. Therefore methods of the invention permit a novel approach to this problem, i.e., the delivery of dopamine for the treatment of Parkinson's disease using encapsulated donor tissue harvested from animals or genetically engineered cells.

Alzheimer's Disease

An estimated 2.5 to 3.0 million Americans are afflicted with Alzheimer's disease. The disease is characterized by a progressive loss of cognitive function associated with degeneration of basal forebrain cholinergic neurons. Studies in animals indicate that Nerve Growth Factor (NGF), e.g., brain-derived neurotrophic factor (BDNF) and neurotrophin-3 (NT-3), available from Regeneron and Amgen, respectively, and other neurotropic factors normally act to support the viability and function of these neuron cells, and that continuous infusion of NGF into the ventricles can prevent injury-induced degeneration of cholinergic neurons as described in Williams et al., *P.N.A.S., USA*, 83:9231 (1986). This treatment correlates with improved cognitive function in rodents with memory impairment as described in Fisher et al., *Neurobiol. Aging*, 10:89 (1989).

These studies suggest that microcapsules containing grafts of recombinant or natural NGF-secreting tissue such as astroglial cells or developing skin, can be used to treat patients suffering from Alzheimer's disease.

Gene Therapy

Gene therapy is an approach to treating a broad range of diseases by delivering therapeutic genes directly into the human body. Diseases that can potentially be cured by gene therapy include diseases associated with the aging population such as cancer, heart disease, Alzheimer's disease, high blood pressure, atherosclerosis and arthritis; viral infectious diseases such as acquired immune deficiency syndrome (AIDS) and herpes; and inherited diseases such as diabetes, hemophilia, cystic fibrosis, and muscular dystrophy.

In one particular example, a favored approach for human gene therapy involves the transplantation of genetically-altered cells into patients, e.g., as described Rosenberg, et al., *New Eng. J Med.*, 323:570–578 (1988). This approach requires the surgical removal of cells from each patient to isolate target cells from nontarget cells. Genes are introduced into these cells via viral vectors or other means, followed by transplantation of the genetically-altered cells back into the patient. Although this approach is useful for purposes such as enzyme replacement therapy (for example, for transplantation into a patient of cells that secrete a hormone that diseased cells can no longer secrete), transplantation strategies are less likely to be suitable for treating diseases such as cystic fibrosis or cancer, where the diseased cells themselves must be corrected. Other problems commonly encountered with this approach include technical problems, including inefficient transduction of stem cells, low expression of the transgene, and growth of cells in tissue culture which can select for cells that are predisposed to cancer.

The methods of the invention are well suited to avoid these problems, because they allow the use of standard human cell lines of, e.g., fibroblast cells, epithelial cells such as HeLa cells, and hepatoma cells such as HepG2, as the implanted cells, rather than requiring the surgical removal of cells from the patient. These cell lines are genetically altered as required by standard techniques and are encapsulated and implanted into the patient. These cell lines are much easier to obtain, culture, and work with than individual patients' cells. Moreover, since the microcapsules prevent the patient's immune system from recognizing and attacking the implanted cells, any human cell lines can be used, making the technique of gene therapy more universally applicable.

Hypoparathyroidism

Acute and chronic symptoms of hypoparathyroidism result from untreated hypocalcemia, and are shared by both hereditary and acquired hypoparathyroidism. The hereditary form typically occurs as an isolated entity without other endocrine or dermatologic manifestations or, more typically, in association with other abnormalities such as defective development of the thymus or failure of other endocrine organs such as the thyroid or ovary. Acquired hypoparathyroidism is usually the result of inadvertent surgical removal of all the parathyroid glands, and is a problem in patients undergoing operations secondary to parathyroid adenoma or hyperplasia. Hypoparathyroidism has been treated in hypocalcemic rats by the administration of microencapsulated parathyroid cells that served as a bioartificial parathyroid. Parathyroid cells can also be encapsulated in microcapsules and used with the methods described herein in administration to animals and human patients.

Osteoporosis

The term osteoporosis covers diseases of diverse etiology that cause a reduction in the mass of bone per unit volume. These diseases can be treated by the administration of microcapsules containing cells that secrete insulin-like growth factor (IGF-1), estrogen in postmenopausal woman to reduce the negative calcium balance and decrease urinary hydroxyproline, androgens in the treatment of osteoporotic men with gonadal deficiency, or calcitonin for use in established osteoporosis.

Reproductive Disorders

There are numerous disorders of the ovary and female reproductive tract that can be treated with progestogens, estrogens, and other hormones. These include progestogen, e.g., progesterone, therapy to inhibit pituitary gonadotropins (precocious puberty in girls), and for prophylaxis to prevent hyperplasia in PCOD. Estrogen therapy is used in the treatment of gonadal failure, control of fertility, and in the management of dysfunctional uterine bleeding. Androgens, gonadotropins, and other hormones are used to treat disorders of the testis, e.g., androgen therapy in hypogonadal men, or gonadotropins to establish or restore fertility in patients with gonadotropin deficiency. Accordingly, these diseases can be treated with microcapsules containing the appropriate hormone-producing cells.

Huntington's Disease

Huntington's disease is characterized by a combination of choreoathetotic movements and progressive dementia usually beginning in midadult life. Distinctive for the disease is atrophy of the caudate nucleus and, to a lesser extent, other structures of the basal ganglia (putamen and globus pallidus). Rodent cells that secrete neurotropic factors have been implanted into the brains of baboons that have a condition similar to Huntington's disease and reversed some of the damaged nerve networks that, in Huntington's patients, lead to progressive loss of control over the body. Similarly, Huntington's disease in human patients can be treated by the administration of microcapsules that contain human or recombinant cells that secrete the appropriate neurotrophic factors.

Spinal Cord Injuries

The majority of spinal cord injuries result from damage to the surrounding vertebral column, from fracture, dislocation, or both. Treatment of such injuries involves the administration of nerve growth factors such as ciliary neurotropic factor (CNTF), insulin-like growth factor (IGF-1), and neurotropic factors, to enhance the repair of the central and peripheral nervous system. Thus, microcapsules containing cells that secrete such factors, either naturally or through genetic engineering, can be used to treat spinal cord injuries.

Mood (or Affective) Disorders

Mood disorders are a group of mental disorders such as schizophrenia characterized by extreme exaggerations and disturbances of mood and affect associated with physiologic (vegetative), cognitive, and psychomotor dysfunctions. Many mood disorders are associated with medical diseases that can be treated with microcapsules containing the appropriate cells such as hypothyroidism, Parkinson's disease, Alzheimer's disease, and malignancies as discussed herein. In addition, it has been shown that the neurotransmitter 5-hydroxyindol acetic acid (5-HIAA), a serotonin metabolite, is reduced in the cerebral spinal fluid of depressed patients. Deficits in other neurotransmitters such as dopamine and $\gamma$-aminobutyric acid (GABA) have also been identified in patients with major depression. Therefore, microcapsules containing cells that secrete these neurotransmitter are useful to treat these deficiencies.

Motor Neuron Diseases

Degenerative motor neuron diseases include ALS (see above), heritable motor neuron diseases such as spinal muscular atrophy (SMA), and those associated with other degenerative disorders such as olivopontocerebellar atrophies and peroneal muscular atrophy. These diseases can be treated by administration of microcapsules containing cells that secrete neurotropic factors like brain-derived neurotrophic factor (BDNF), and neurotrophin-3 (NT-3).

Acquired Immunodeficiency Syndrome (AIDS)

AIDS is caused by an underlying defect in cell-mediated immunity due to the human immunodeficiency virus (HIV), and causes persistent constitutional symptoms and/or diseases such as secondary infections, neoplasms, and neurologic disease. Patients can be treated to ameliorate symptoms by immunologic augmentation with microcapsules that contain cells genetically engineered to secrete, e.g., recombinant human IL-2 (to decrease suppressor cell activity resulting in an increased T cell adjuvant activity); or recombinant human INF-$\gamma$ (macrophage augmentation). AIDS-related tumors such as Kaposi's sarcoma can be treated with encapsulated cells that secrete human interferon-$\alpha$, interleukin-2 and tumor necrosis factor (TNF).

Amyotrophic Lateral Sclerosis (Lou Gehrig's Disease)

ALS is the most frequently encountered form of progressive motor neuron disease, and is characterized by progressive loss of motor neurons, both in the cerebral cortex and in the anterior horns of the spinal cord, together with their homologs in motor nuclei of the brainstem. ALS can be treated with microcapsules that contain cells that secrete nerve growth factors such as myotrophin, insulin-like growth factor (IGF-1), ciliary neurotropic factor (CNTF), brain-derived neurotrophic factor (BDNF) and neurotrophin-3 (NT-3). Animal studies with these factors (IGF-1 is available from Cephalon, CNTF from Regeneron, and NT-3 from Amgen), have demonstrated that they can stem the degenerative effects caused by nerve damage or disease.

Cancer

In most cases, cancer originates from a single stem cell which proliferates to form a clone of malignant cells. Growth is not properly regulated by the normal biochemical and physical influences in the environment. There is also a lack of normal, coordinated cell differentiation. Cancer cells develop the capacity for discontinuous growth and dissemination to other parts of the body.

Various cancers can be treated according to the invention by the administration of microcapsules containing cells that secrete interferon-$\alpha$ (IFN-$\alpha$) (for solid tumors, hairy cell leukemia, Kaposi's sarcoma, osteosarcoma, and various lymphomas); recombinant interleukin-2 (IL-2) (for melanoma, renal carcinoma, and Kaposi's sarcoma); tumor necrosis factor (with IL-2 for Kaposi's sarcoma); recombinant human IFN-$\alpha$ and recombinant human colony stimulating factor-granulocyte macrophage (GM-CSF) (for Kaposi's sarcoma); recombinant human INF-$\gamma$ (for macrophage augmentation); CSF (for aggressive chemotherapy, bone marrow transplantation, priming of leukemic cells to enhance sensitivity to chemotherapy and to support dose intensification); ciliary neurotropic factor (CNTF) and insulin-like growth factor (IGF-1) (for peripheral neuropathies caused by chemotherapy); adrenal gland cells (for pain relief when injected into the lower spine to secrete natural painkillers) and progesterone-producing cells (for palliation in endometrial and breast carcinoma).

Duchenne's Muscular Dystrophy

Duchenne's dystrophy is an X-linked recessive disorder characterized by progressive weakness of girdle muscles, inability to walk after age 12, kyphoscoliosis (curvature of the spine), and respiratory failure after the fourth decade. This disease can be treated by administration of microcapsules containing myoblast cells and growth factors. Myoblasts have been injected into young boys with Duchenne's muscular dystrophy to determine whether the cells can supply a structural protein that is missing. Researchers have observed muscle strength improvement in several of the boys.

Epilepsy

The epilepsies are a group of disorders characterized by chronic, recurrent, paroxysmal changes in neurologic function caused by abnormalities in the electrical activity of the brain. In some forms of focal epilepsy, inhibitory interneurons appear to be preferentially lost. Treatment with neurotropic factors and other neuropeptides such as has been found effective. Therefore, the microcapsules containing cells secreting these factors can be used to treat epilepsy.

It is to be understood that while the invention has been described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

All patents and publications referred to herein are hereby incorporated by reference.

What is claimed is:

1. A method of inhibiting the fibrotic inactivation, by a subject, of an implantable device which contains a cell, comprising:

administering to a subject into which an implantable device which contains a cell has been implanted, an effective amount of a non-steroidal anti-inflammatory agent to the subject, thereby inhibiting fibrotic inactivation of said device.

2. The method of claim 1, wherein said cell is from a species other than the subject.

3. The method of claim 2, wherein said device is a microcapsule which comprises a hydrogel.

4. The method of claim 3, wherein said hydrogel comprises agarose or alginate.

5. The method of claim 4, wherein said gel is alginate and has a higher number of guluronic acid than mannuronic acid monomers.

6. The method of claim 3, wherein said microcapsule comprises a semipermeable membrane.

7. The method of claim 6, wherein said semipermeable membrane comprises a positively charged polymer.

8. The method of claim 7, wherein said positively charged polymer comprises a polyamino acid.

9. The method of claim 8, wherein said positively charged polymer comprises lysine or ornithine.

10. The method of claim 9, wherein said positively charged polymer is polylysine.

11. The method of claim 3, wherein said microcapsule comprises chitosan.

12. The method of claim 1, wherein said cell is a pancreatic islet cell.

13. The method of claim 12, wherein said pancreatic islet cell is from a pig, a goat, a sheep, a horse, a cow, or a non-human primate.

14. The method of claim 12, wherein said pancreatic islet is from a pig.

15. The method of claim 1, wherein said cell is a genetically engineered cell.

16. The method of claim 1, wherein said cell is from an adrenal gland, brain, kidney, liver, thymus, parathyroid, or thyroid gland.

17. The method of claim 1, wherein said cell is a cultured cell.

18. The method of claim 1, wherein said cell is a fetal cell.

19. The method of claim 1, wherein said non-steroidal anti-inflammatory agent comprises a carboxylic acid or an enolic acid.

20. The method of claim 1, wherein said non-steroidal anti-inflammatory agent comprises a pyrazolone or a xicam.

21. The method of claim 1, wherein said non-steroidal anti-inflammatory agent comprises a salicylate, a proprionate, an anthranilate or a phenylacetate.

22. The method of claim 1, wherein said non-steroidal anti-inflammatory agent comprises naproxen.

23. The method of claim 1, wherein said subject is a primate.

24. The method of claim 1, wherein said subject is a human and said cell is from a second species.

25. The method of claim 24, wherein said second species is selected from the group consisting of a simian, a pig, a sheep, a goat, a cow, a goat, a horse, and a dog.

26. The method of claim 24, wherein said second species is concordant.

27. The method of claim 24, wherein the second species is a primate.

28. The method of claim 1, wherein the subject and the cell are from the same species.

29. A method of inhibiting fibrotic inactivation, by a subject, of an implantable microcapsule which includes a xenogeneic cell embedded in a gel core which is enclosed with a semipermeable membrane, comprising: administering an effective amount of a non-steroidal anti-inflammatory agent, thereby inhibiting fibrotic inactivation.

30. The method of claim 29, wherein the non-steroidal anti-inflammatory agent comprises administration of at least one of the group consisting of aspirin, naprosyn, and acetaminophen.

* * * * *